US006979305B2

(12) United States Patent
Porrata et al.

(10) Patent No.: US 6,979,305 B2
(45) Date of Patent: *Dec. 27, 2005

(54) APPARATUS AND METHOD FOR TREATING CARPAL TUNNEL SYNDROME

(75) Inventors: Humberto L. Porrata, Ft Lauderdale, FL (US); Alejandro A. Porrata, New York, NY (US)

(73) Assignee: Porrata Group, LLC, Ft. Lauderdale, FL (US)

(*) Notice: Subject to any disclaimer, the term of this patent is extended or adjusted under 35 U.S.C. 154(b) by 0 days.

This patent is subject to a terminal disclaimer.

(21) Appl. No.: 10/199,747

(22) Filed: Jul. 18, 2002

(65) Prior Publication Data

US 2003/0018286 A1  Jan. 23, 2003

Related U.S. Application Data

(63) Continuation-in-part of application No. 09/908,154, filed on Jul. 18, 2001, now abandoned.

(51) Int. Cl.[7] .................................................. A61F 5/00
(52) U.S. Cl. ........................... 602/21; 602/6; 602/13; 128/879
(58) Field of Search .............................. 602/5, 6, 8, 12, 602/13, 20–23, 26, 27, 60–64; 128/878, 879, 128/DIG. 20

(56) References Cited

U.S. PATENT DOCUMENTS

| | | |
|---|---|---|
| 2,388,330 A | 11/1945 | Jungmann |
| 2,823,668 A | 2/1958 | Van Court et al. |
| 2,943,859 A | 7/1960 | Koski |
| 4,067,063 A | 1/1978 | Ettinger |
| 4,378,009 A | 3/1983 | Rowley et al. |
| 4,479,648 A | 10/1984 | Alivo |
| 4,787,376 A | 11/1988 | Eisenberg |
| 4,899,763 A | 2/1990 | Sebastian |
| 4,941,460 A | 7/1990 | Working |
| 5,014,689 A | 5/1991 | Meunchen et al. |
| 5,029,573 A | 7/1991 | Chow |
| 5,152,302 A | 10/1992 | Fareed |
| 5,256,136 A | 10/1993 | Sucher |
| 5,279,545 A * | 1/1994 | Reese, Sr. .................... 602/21 |
| 5,297,541 A * | 3/1994 | Hensey ........................ 601/40 |
| 5,366,436 A | 11/1994 | Gibney |
| 5,385,537 A | 1/1995 | Davini |
| 5,405,357 A | 4/1995 | Rowe-Lanzisera et al. |
| 5,413,553 A | 5/1995 | Downes |

(Continued)

FOREIGN PATENT DOCUMENTS

EP         0 861 651 A1      9/1998

(Continued)

*Primary Examiner*—Michael A. Brown
*Assistant Examiner*—Quang D. Thanh
(74) *Attorney, Agent, or Firm*—Bryan Cave LLP

(57) ABSTRACT

An apparatus for treating carpal tunnel syndrome in a patient's hand includes a bilateral housing for receiving the patient's right or left hand with two bottom capture regions for capturing and retaining the thenar and hypothenar regions of the patient's hand. The housing also includes a top portion with a pressure element adapted and configured to contact at least a portion of the central longitudinal dorsal region of the patient's hand. The pressure element is connected to a pressure source, such that when the hand is inserted into the housing, the pressure element may be activated to exert pressure on the respective central dorsal region of the hand while the hypothenar and thenar regions of the band are retained by the first and second capture regions, thus exerting forces opposite to the pressure exerted by the pressure element.

21 Claims, 4 Drawing Sheets

U.S. PATENT DOCUMENTS

| | | | |
|---|---|---|---|
| 5,417,645 A | 5/1995 | Lemmen | |
| 5,438,726 A * | 8/1995 | Leite | 15/105 |
| 5,441,058 A | 8/1995 | Fareed | |
| 5,468,220 A | 11/1995 | Sucher | |
| 5,584,854 A | 12/1996 | Minarik | |
| 5,613,941 A | 3/1997 | Prengler | |
| 5,647,850 A | 7/1997 | Allen | |
| 5,672,150 A | 9/1997 | Cox | |
| 5,702,355 A | 12/1997 | Repice et al. | |
| 5,707,345 A | 1/1998 | Fulk | |
| 5,810,753 A | 9/1998 | Eberbach | |
| 5,897,549 A | 4/1999 | Tankovich | |
| 5,916,185 A * | 6/1999 | Chitwood | 602/18 |
| 5,916,187 A | 6/1999 | Brill | |
| 5,925,007 A | 7/1999 | Ashline | |
| 5,950,628 A | 9/1999 | Dunfee | |
| 6,029,277 A | 2/2000 | Picchione, II | |
| 6,120,472 A | 9/2000 | Singer, Jr. | |
| 6,146,347 A | 11/2000 | Porrata | |
| 6,179,800 B1 | 1/2001 | Torrens | |
| 6,200,286 B1 | 3/2001 | Zamani | |
| 6,213,969 B1 | 4/2001 | MacMorran et al. | |
| 6,217,536 B1 | 4/2001 | Gustafson | |
| 6,264,621 B1 | 7/2001 | Paske | |
| 6,290,662 B1 * | 9/2001 | Morris et al. | 601/149 |
| 2002/0072786 A1 | 6/2002 | Gordon | |
| 2003/0028136 A1 | 2/2003 | Stager | |
| 2003/0125652 A1 | 7/2003 | Porrata | |
| 2003/0130604 A1 | 7/2003 | Porrata | |
| 2003/0130690 A1 | 7/2003 | Porrata | |
| 2003/0130691 A1 | 7/2003 | Porrata | |
| 2003/0130692 A1 | 7/2003 | Porrata | |

FOREIGN PATENT DOCUMENTS

| WO | WO 97 23176 A | 7/1997 |
|---|---|---|

\* cited by examiner

APPARATUS AND METHOD FOR TREATING CARPAL TUNNEL SYNDROME

RELATED APPLICATION

This application is a continuation-in-part of the commonly assigned U.S. patent application Ser. No. 09/908,154 entitled "Bilateral Appliance and Method for Treating Carpal Tunnel Syndrome" which was filed on Jul. 18, 2001 now abandoned.

FIELD OF THE INVENTION

This invention relates generally to treatment of carpal tunnel syndrome, and more particularly to a non-invasive apparatus and method for treatment of carpal tunnel syndrome.

BACKGROUND OF THE INVENTION

Carpal tunnel syndrome is a physiological disorder that afflicts over 850,000 people each year in the United States alone. In order to better understand the cause of the carpal tunnel syndrome and the difficulty in treating this serious disorder, a detailed explanation of the physiological factors and causes of carpal tunnel syndrome is presented below. Carpal tunnel syndrome is caused by a deleterious increase in pressure on the median nerve which passes through the carpal tunnel (or canal) in the hand, adjacent to the wrist. The deleterious increase in pressure, which is commonly brought on by prolonged repetitive motion of the hand and digits, is often caused by inflammation or damage to tendons for the hand which pass through the carpal tunnel along with the median nerve. Pressure increases can also be caused by narrowing of the carpal canal, and by generalized swelling of the structures in the hand. Thus, when the carpal tunnel is narrowed from ligament shortening, muscle development or structural inflammation, the median nerve is undesirably compressed.

Referring to FIG. 7, the carpal tunnel is formed by the eight carpal bones of the hand adjacent the wrist, which bones are arranged in two rows forming a generally U-shaped inverted arch-like "tunnel" structure. The three large carpal bones of the proximal row (i.e., closest to the chest), beginning laterally (i.e., from the outside with the hand directed downward and the palm facing forward), are the scaphoid, lunate, and triquetrum; the smaller pisiform bone sits on the palmar surface of the triquetrum. The distal row, from lateral to medial, consists of the trapezium, trapezoid, capitate, and hamate carpal bones. The vault of the carpal tunnel is formed by the carpal ligament and the flexor retinaculum. Nine tendons, their tendon sheaths, and the median nerve pass through the tunnel.

The carpal ligament is made of collagen and elastin and extends from the pisiformis and hamulus of hamate bones on the ulnar aspect of the tunnel to the tubercle (i.e., projection) of trapezium and the tubercle of the scaphoid bones on the radial (i.e. lateral) aspect of the carpal tunnel. The flexor retinaculum also stretches across the carpal tunnel and attaches to, on the medial aspect of the carpal tunnel, the pisiform bone and the hook of hamate, and, on the lateral aspect, the tubercle of the scaphoid and trapezium bones. The proximal border of the flexor retinaculum corresponds generally to the transverse skin crease at the base of the hand/wrist. The carpal ligament and flexor retinaculum, along with the carpal bones, form the restricted space through which the median nerve and several tendons pass.

Symptoms of carpal tunnel syndrome include tingling sensation in the hand, discomfort, numbness, and pain localized in the hand or radiating up the arm to the shoulder. All of these symptoms can occur during the day or can make the patients wake up at night. In advanced cases, there is atrophy and weakness of the thenar area of the hand which may weaken the grip and cause objects to fall out of the hand.

Conventional treatment of carpal tunnel syndrome is divided into surgical (invasive) and conservative (non-invasive). Surgical treatment consists of making an incision on the palmar aspect of the hand and splitting the carpal ligament, thus partially opening the carpal tunnel and relieving the pressure. This procedure, while occasionally successful, often has negative consequences, which include, but are not limited to, non-resolution of symptoms often requiring a second surgery, pain in the area of the scar, and injury to the superficial palmar branch of the median nerve causing persistent neurologic symptoms such as loss of full control over the hand. Furthermore, this procedure is very expensive. Understandably, surgical treatment is often considered as a last option.

Conservative, non-invasive treatment is typically separated into three categories—mild, moderate and alternative. Mild treatments may involve the use of anti-inflammatory medications, application of resting hand splints, physical therapy, modification of patient's activities that cause the condition, and even a change in the patient's job. Moderate treatments involve one or more mild treatments coupled with cortisteriod injections. Finally, alternative methods include acupuncture, massage, application of magnets, tai-chi exercises, and the like.

However, none of the above treatments have produced uniformly positive results. While some treatments may alleviate the symptoms of carpal tunnel syndrome in individual patients, the symptoms often return when the course of treatment is terminated. Furthermore, one of the main disadvantages of the various treatment approaches is that they must be delivered by a healthcare provider such as a physician or a physical or occupational therapist. This adds a significant level of inconvenience to the patient who must allocate time to visit the healthcare provider for injections and/or physical therapy. Medications that are used to provide relieve from the pain and discomfort caused by carpal tunnel syndrome also suffer from a number of disadvantages. For example, certain medications have undesirable side effects or interactions with the patient's other medications, if any.

As a result, a number of techniques for treating carpal tunnel syndrome that address at least some of the above problems have been developed over the years. Some merely maintain the patient's hand in a neutral position (such as the device disclosed in U.S. Pat. No. 5,014,689) to prevent the symptoms from worsening. Another approach involved mechanical stretching of the carpal ligament, as disclosed in U.S. Pat. No. 5,256,136. Yet another series of techniques advocated placement of a compression bracelet on the forearm (U.S. Pat. No. 5,441,058), or on the wrist (U.S. Pat. No. 5,468,220) to apply a predetermined pressure on certain portions of the forearm, or wrist, respectively, in order to widen the carpal tunnel and thus provide relief to the patient suffering from carpal tunnel syndrome.

Other approaches involved construction of a wrist brace with palm support to immobilize the wrist while applying force to the entire palmar aspect of the hand via a dome positioned on a lower portion of the splint (U.S. Pat. No. 5,672,150). However, the above-described previously known devices suffer from a crucial disadvantage. Application of pressure to different portions of the forearm and/or the wrist only has a minimal effect on widening the carpal tunnel, and may only provide temporary relief from carpal tunnel syndrome rather than eliminating or suppressing the condition.

One technique disclosed in U.S. Pat. No. 6,217,536 taught dorsally directed force to the palm of a patient's hand to cause compression of the palmar region. While this approach provides some relief from the discomfort of the carpal tunnel syndrome, its configuration does not force improvement in the condition of the portions of the patient's hand and wrist that have the strongest effect on the continual suffering from the carpal tunnel syndrome.

Further development in the area of mechanical treatment of carpal tunnel syndrome continued, and eventually resulted in discovery of the Porrata principle, disclosed in the commonly assigned U.S. Pat. No. 6,146,347 to Humberto Porrata, that provides novel and advantageous device and method for treating carpal tunnel syndrome that solve the problems posed by previously known devices and techniques. Most importantly, research conducted in conjunction with development of the Porrata device, has shown that carpal tunnel syndrome may be treated with great effectiveness by precise controlled transverse stretching of the carpal ligament and the flexor retinaculum. The U.S. Pat. No. 6,146,347 patent disclosed a splint-like device that fit over the patient's hand and a portion of the wrist. The device included rigid sections for contacting the thenar and hypothenar portions of the hand and a selectable active pressure source that, when actuated, applied pressure to the dorsal portion of the patient's hand opposed by the forces delivered by the thenar and hypothenar sections of the device in such a manner, as to transversely stretch the carpal ligament and the flexor retinaculum in a comfortable and controlled manner.

Nevertheless, the device of the U.S. Pat. No. 6,146,347 patent had one main drawback. Because of it's splint-like construction it had to be fabricated in different sizes to fit various patients, and patients with unusual hand sized or shapes would need custom-fabricated devices. Similarly, separate devices would need to be manufactured for right- and left-handed patients.

It would thus be desirable to provide an apparatus and method for treating carpal tunnel syndrome by stretching the carpal ligament and the flexor retinaculum of a patient's hand in a comfortable and controlled manner. It would further be desirable to provide an apparatus and method for treating carpal tunnel syndrome embodied in a device that is dynamically adaptable to patients of various physical characteristics and capable on being used by right- and left-handed patients. It would also be desirable to provide an apparatus and method for treating carpal tunnel syndrome embodied in a device that is easy and inexpensive to manufacture.

SUMMARY OF THE INVENTION

The apparatus and method of the present invention advantageously overcome the problems and drawbacks of previously known approaches for treating carpal tunnel syndrome. Similarly to the device disclosed in the commonly assigned U.S. Pat. No. 6,146,347 which is hereby incorporated by reference in its entirety, the main objective of the present invention is to apply the Porrata principle to transversely stretch the carpal ligament and the flexor retinaculum, as well as the superficial structures and muscles of the hand, in a safe manner under precise control of the patient or a healthcare professional. However, the apparatus and method of the present invention enable the Porrata principle to be implemented in a device that may be readily used by patients with any size or shape hands. Furthermore, the inventive apparatus is very simple and inexpensive to manufacture.

Controlled and monitored use of the inventive apparatus dynamically treats carpal tunnel syndrome through the active application of pressure to large portions of the palm of the hand (in the thenar and hypothenar areas) while at the same time retaining and leveraging a large portion of the dorsum of the hand, in essence providing pressure in the opposite direction. This procedure transversely stretches the carpal ligament, the flexor retinaculum, and superficial structures and muscles of the hand in the palmar aspect of the hand, in a readily, safely controllable and comfortable manner.

Considering that the constitutions of the carpal ligament and the flexor retinaculum are soft tissue composed of collagen and elastin, stretching the carpal ligament and the flexor retinaculum is effective for decreasing compression on the median nerve by increasing the diameter of the tunnel and decreasing the rigidity of the retinaculum and the carpal ligament, thus alleviating the symptoms of carpal tunnel syndrome.

Various embodiments of the inventive apparatus commonly include an elongated housing for receiving the patient's hand, the housing having an opening at each end, a bottom portion having a thenar capture region adapted and configured to contact and retain the thenar region of the patient's hand, and a hypothenar capture region adapted and configured to contact and retain hypothenar region of the patient's hand when the patient inserts their hand through one of the openings, and a top portion having a central longitudinal pressure element adapted and configured to contact at least a portion of the central longitudinal dorsal region of the patient's hand. A hole sized and configured to accept a patient's thumb is defined in the thenar side of the housing. Due to the bilateral construction of the housing, the patient has the ability to insert their hand into either opening in the housing (depending on whether the hand to be treated is the right and or the left hand) such that their thumb is guided through the hole and their thenar and hypothenar regions are contacted and retained by the first and second capture regions. While the housing may include a longitudinal open region between the first and second capture regions, optionally, the open region may be covered by a resilient element connecting the first and second capture regions.

In a first embodiment of the present invention, the pressure element is connected to active pressure source (provided separately from the housing and connected thereto, or disposed on the housing itself), such that when the hand is inserted into the housing, the pressure element may be activated to exert pressure on the respective central dorsal region of the hand while the hypothenar and thenar regions of the hand are disposed within and retained by the first and second capture regions, thus exerting forces opposite to the pressure exerted by the pressure element. This forces the thenar and hypothenar regions apart, thus, advantageously transversely stretching the carpal ligament, the flexor retinaculum, and superficial structures and muscles of the hand. In another embodiment of the present invention, an optional pressure monitor is connected to the pressure element to enable the patient or medical practitioner to monitor the use of the inventive apparatus. The pressure monitor may include an optional timer to further facilitate the delivery of properly monitored treatment to the patient.

In another embodiment of the invention, one or more heating elements may be disposed within the housing to apply heat to predefined regions of the patient's hand during treatment. For example, a heating element may be disposed between the first and second capture regions along a central longitudinal portion of the patient's hand. Another heating element may be disposed along the pressure element itself to apply heat to the dorsal aspect of the patient's hand. Applying heat to various regions of the hand during treatment advantageously improves muscle elasticity and improves the effectiveness of the treatment. The heating elements may be simple heated members (or members coated with a heat-inducing substance) or active heated elements connected to a heat delivery device and controller.

Because of the bilateral construction of the housing and because the pressure element is adjustable and configurable (by varying the magnitude of pressure delivered by the pressure source), the inventive apparatus is readily usable by patients with different hand shapes and/or sizes to prevent progression of carpal tunnel syndrome and to provide relief from symptoms by increasing the cross sectional area of the carpal tunnel, thus decreasing compression on the median nerve and decreasing the resulting symptoms.

Other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims.

BRIEF DESCRIPTION OF THE DRAWINGS

In the drawings, wherein like reference characters denote like elements throughout the several views.

DETAILED DESCRIPTION OF PREFERRED EMBODIMENTS

The present invention is described with reference to various materials that compose the inventive structures and elements thereof, and to various devices for selectively applying pressure to specific areas of the hand, by way of example only—it should be understood that the apparatus and method of the present invention may be utilized with any materials or selective pressure sources having properties similar to those described in the exemplary embodiments, without departing from the spirit of the invention.

The essence of the Porrata approach, disclosed and described in greater detail in the above-incorporated U.S. Pat. No. 6,146,347, involves applying pressure to a portion of the top surface of the hand (i.e., the central dorsal region), while at the same time applying opposing pressure to the thenar and hypothenar regions of the palm. The apparatus and method of the present invention advantageously implement the Porrata principle in a simple to use device that works equally well with different hand shapes and sizes.

Figure 1A:
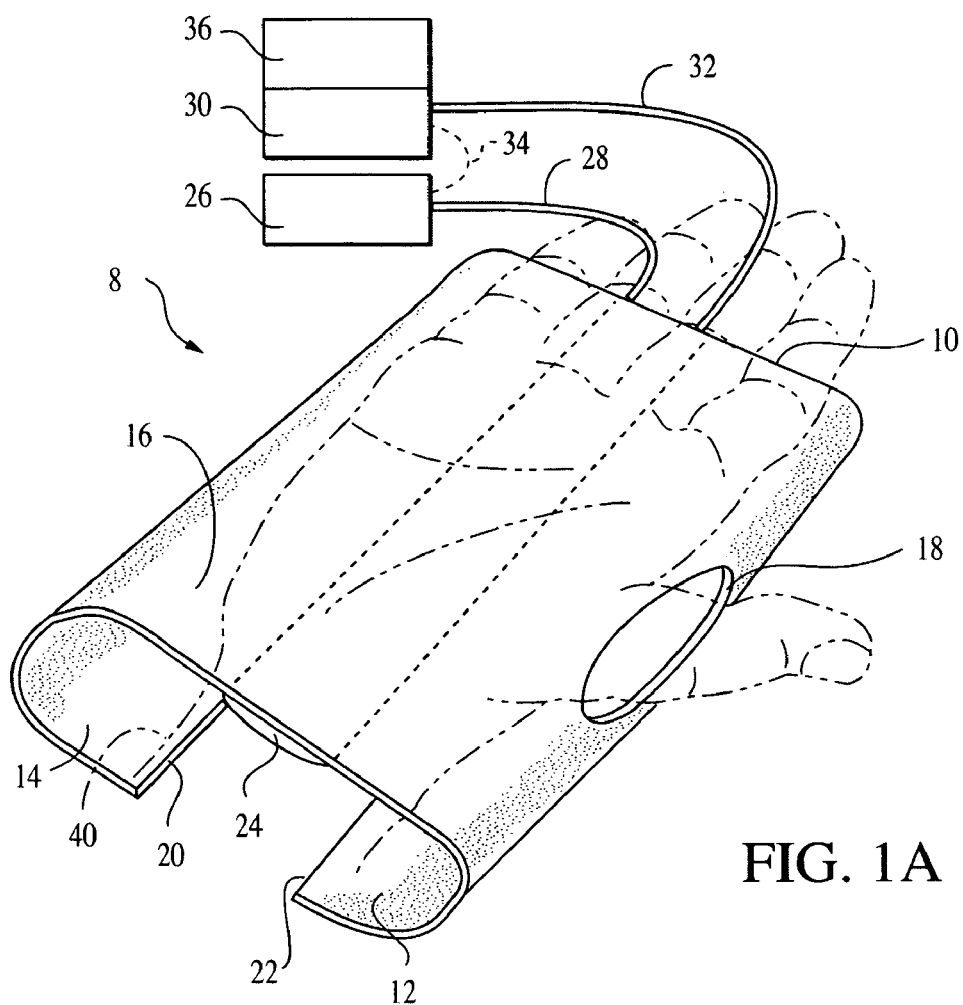
FIG. 1A is an isomeric view of a first embodiment of the inventive apparatus for treating carpal tunnel syndrome.

Referring now to FIG. 1A, a first embodiment of an inventive apparatus 8 is shown. The apparatus 8 is substantially C-shaped and includes a housing 10 having a thenar section 12 for contacting and retaining the thenar region of a hand 40, a hypothenar section 14 for contacting and retaining the hypothenar region of the hand 40, and a dorsal section 16 connecting the top regions of the thenar and hypothenar sections 12, 14. The thenar, hypothenar, and dorsal sections 12, 14, and 16 of the housing 10 are preferably integrally formed (but may optionally be formed from separate connected sections) and are sized and shaped to conform to the shape of the associated areas of the hand 40. The housing 10 may be composed of a rigid material such as metal, hard plastic or wood, or a semi-resilient material such as fiberglass or resilient plastic, or a combination thereof. Optionally, the housing 10 may include a plurality of ventilation openings (not shown) to provide ventilation to the hand 40 during the operation of the apparatus 8. The thenar section 12 preferably includes a hole 18 shaped and positioned for receiving the patient's thumb.

The apparatus 8 may be manufactured in general "small-medium-large" sizes, each for a limited range of hand shapes and sizes. However, the apparatus 8 can be individually sized for each user by using the patient's hand as a model or mold.

Figure 1B:
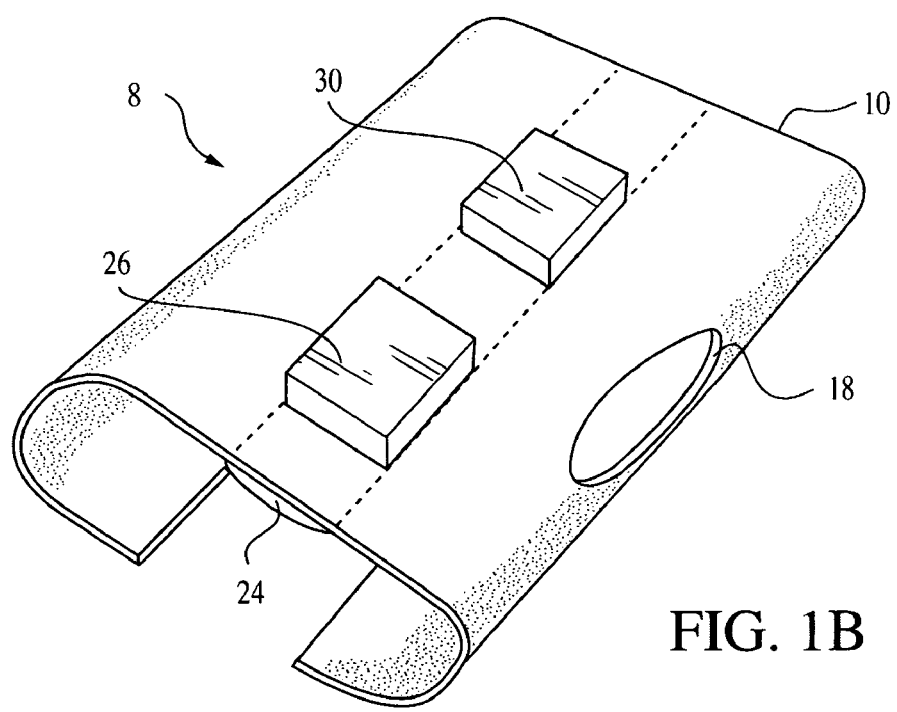
FIG. 1B is an isometric view of an alternate embodiment of the inventive apparatus of FIG. 1A.

The apparatus 8 also includes a pressure element 24 positioned along the dorsal section 16 for contacting and selectively exerting pressure on the longitudinal central dorsal portion of the hand during treatment. The thenar section 12 includes an edge 22 that contacts the thenar region of the hand 40, while the hypothenar section 14, includes a corresponding and opposed edge 20 that contacts the hypothenar region of the hand 40, The edges 20, 22 may be positioned such that they substantially correspond to the longitudinal boundaries of the pressure element 24. The pressure element 24 is connected, via a connector 28, to a pressure source 26 for selectively activating and de-activating the pressure element 24. Preferably, the pressure source 26 includes a pressure limiting device (not shown) to limit the maximum magnitude of pressure that can be delivered by the pressure element 24. An optional pressure indicator 30, for monitoring the magnitude of pressure being delivered to the hand 40 by the pressure element 24 during treatment, may be connected to the pressure element 24 via a connector 32 or, alternately, connected directly to the pressure source 26 via a connector 34. An optional timer 36 may be positioned proximal to the pressure indicator 30 (or optionally proximal to any other component of the apparatus 8) for monitoring the length of the treatment with the apparatus 8. Optionally, the timer 36 may be supplied with a count-down feature and an alarm so that the patient or the medical practitioner can select an appropriate length of treatment and be automatically alerted by the timer 36 when the end of treatment is reached. Referring to FIG. 1B, alternately, the pressure source 26 and/or the pressure monitor 30 may be positioned proximal to the outer surface of the housing 10, and directly connected to the pressure element 24 without the use of the respective connectors 28, 32.

The pressure element 24 may be any selectively controllable (singular or plural) pressure element such as air or fluid inflatable bladder, a mechanical pressure plate, an electromechanical pressure plate actuated by a solenoid or the like, or a combination thereof. The pressure source 26 (and the connector 28) and the pressure monitor 30 (and the connectors 32 or 34) must be selected to correspond to the type and configuration of the particular pressure element 24 being used to provide the necessary pressure delivery and control. For example, if the pressure element 24 is an air-inflatable bladder, the pressure source 26, is an air pump, the connector 28 is an air hose, and the pressure monitor 30 is a pressure gauge. In another example, if the pressure element is an electromechanically actuated plate (for example, using a solenoid), the pressure source 26 is an electrical power source (and the connector 28 is a wire), and the pressure monitor 30 is an electronic readout. In this example, control over the delivered pressure is actuated by varying the electrical power delivered by the electrical power source.

Figure 2:
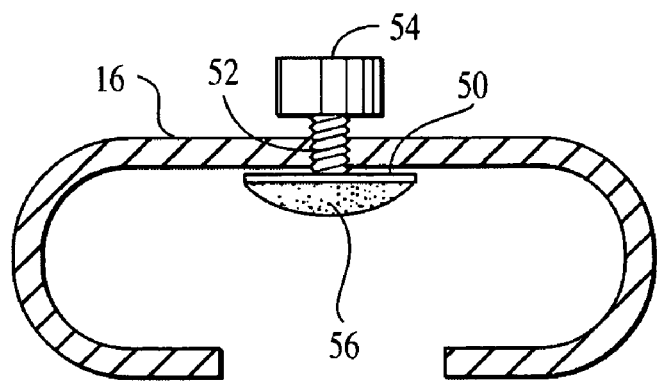
FIG. 2 is a cross-section view of another embodiment of the inventive apparatus of FIG. 1A.

In yet another example, shown in FIG. 2, the pressure element 24 is a mechanically actuated plate 50 and the pressure source 26 is a threaded fastener mechanism 52 connecting the plate 50 to the dorsal section 16 through a complimentary threaded hole 54 in the dorsal section 16, whereby rotation of the threaded fastener mechanism 52 urges the pressure plate alternately away from or toward the dorsal section 16. The threaded fastener mechanism 52 includes a gripping portion 56, accessible by the user when the apparatus 8 is in use, to permit adjustment of the pressure applied to the hand 40 by the pressure plate 50. Also preferably, a resilient pad 58 is affixed to the pressure plate 50 in a position to contact the central dorsal region of the hand 40 to distribute the force applied thereto and to improve comfort during treatment.

Other types of active pressure elements, and corresponding pressure sources, may be utilized as a matter of design choice without departing from the spirit of the present invention.

Figure 3:
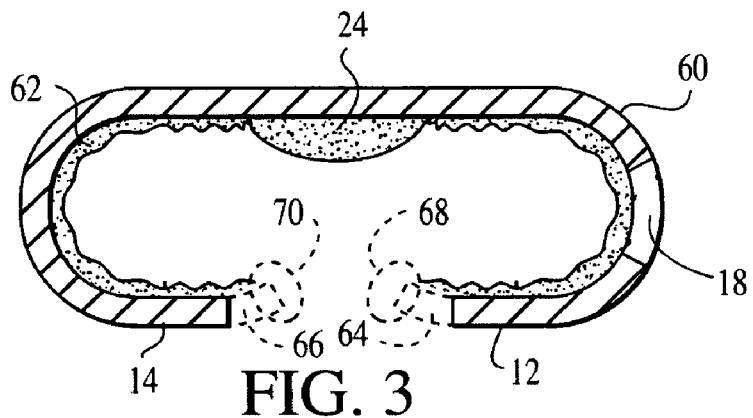
FIG. 3 is a cross-section view of another embodiment of the inventive apparatus of FIG. 1A.

Referring now to FIG. 3, an alternate embodiment of the housing 10 of FIG. 1A is shown as a housing 60. The housing 60 includes a resilient cushion material 62 positioned along the interior surfaces of the thenar, hypothenar, and dorsal sections 12, 14, 16 to further distribute the forces applied to the hand 40 and to increase the comfort of the apparatus 8. Preferably, the cushion material 62 extends substantially the entire length of the respective section, i.e., from one end to the other, such that the cushion material is effective when using the apparatus 8 on either hand. Alternately, only certain selected portions of the housing 60 may be provided with the cushion material 62. The cushion material 62 can be cloth padding, rubber, silicone, gel, or the like. The housing 60 may also include one or both optional curved edges 64, 66 provided along edges of the respective thenar and hypothenar sections 12, 14. The curved edges 64, 66 are angled toward the palmar aspect of the patient's hand and provide improved retention of the respective thenar and hypothenar regions of the hand during treatment. Optional resilient rim members 68, 70 may be provided along the respective curved edges 64, 66 to further improve patient comfort during treatment and to prevent the curved edges 64, 66 from causing discomfort to the patient's palm.

Figure 4:
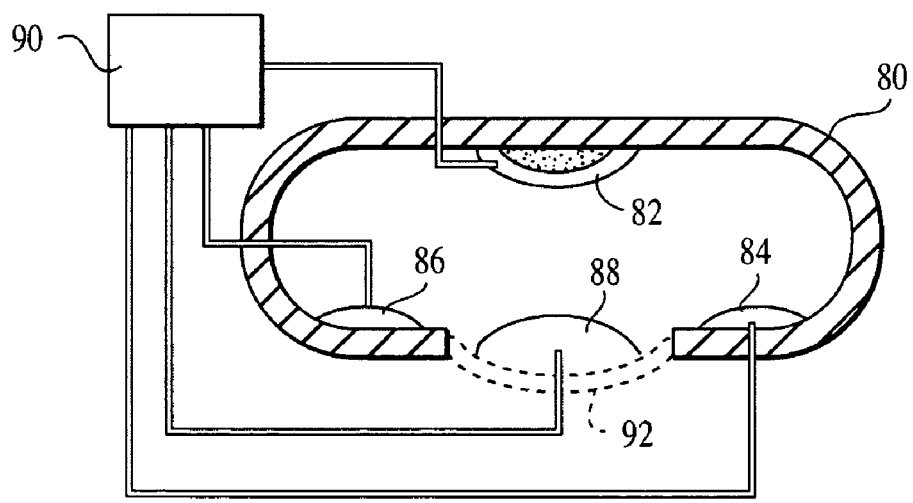
FIG. 4 is a cross-section view of another embodiment of the inventive apparatus of FIG. 1A.

Referring now to FIG. 4, an alternate embodiment of the apparatus 8 is shown as an apparatus 80. The apparatus 80 includes one or more heating elements disposed within the housing 10 to provide therapeutic heat to the patient's hand during treatment. For example, a heating element 82 may be provided on the dorsal section 16 proximal to, or on the pressure element 24, and optional heating elements 84, 86 may be provided along respective thenar and hypothenar sections 12, 14. Preferably, a resilient member 92 connects the thenar and hypothenar sections 12, 14 along the palmar aspect of the hand and a heating element 88 is positioned along the, resilient member 92 to deliver therapeutic heat to the most important portion of the patient's hand during treatment to improve elasticity of the muscles and ligaments and to improve comfort during treatment.

The heating elements 82, 84, 86, 88 may be passive heat-retaining elements heated prior to treatment and inserted into desired positions in the housing 10, or optionally may be active heating elements such as coated electric coils connected to a heat source 90 (such as an electric power source). Preferably, the heat source 90 includes a controller for controlling delivery of therapeutic heat during treatment and a limiting device for limiting heat to safe temperature levels.

Returning now to FIG. 1A, to utilize the apparatus 8, a patient inserts their hand 40 into the housing 10, such that the thenar region of the patient's palm is contacted by and retained in the thenar section 12 (the patient's thumb passing through the hole 18), the hypothenar region of the palm is contacted by and retained in the hypothenar section 15, while the dorsal section 16 is aligned with the dorsal aspect of the hand 40, such that a deactivated pressure element 24 is positioned along and contacts the longitudinal central dorsal region of the hand 40 (between the thenar and hypothenar regions). Because the apparatus 8 is bilateral, the patient can insert their right hand or their left hand into the housing 10 as long as the above conditions for contacting the appropriate regions of the hand by the various sections of the apparatus 10 are met.

Figure 5:
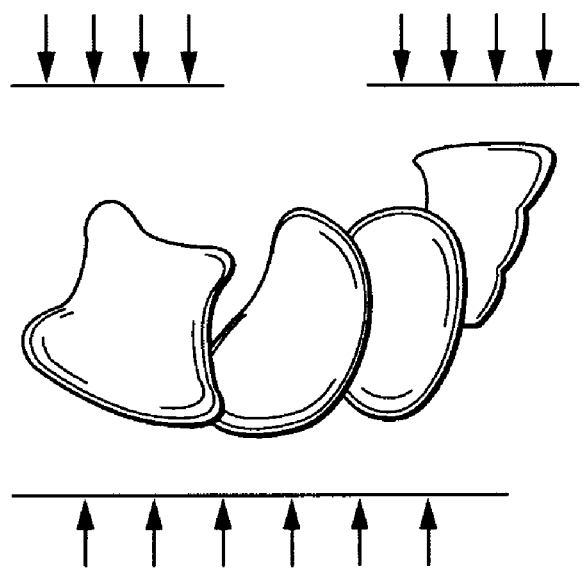
FIG. 5 is a proximal end elevational schematic view of the carpal bones of the hand subject to forces applied by the inventive apparatus of FIG. 1A
Figure 6:
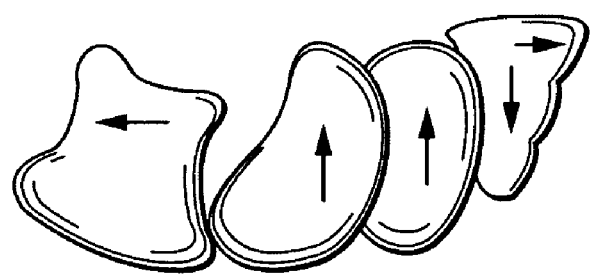
FIG. 6 is a proximal end elevational schematic view of the carpal bones of the hand as displaced by the forces indicated in FIG. 5.
Figure 7:
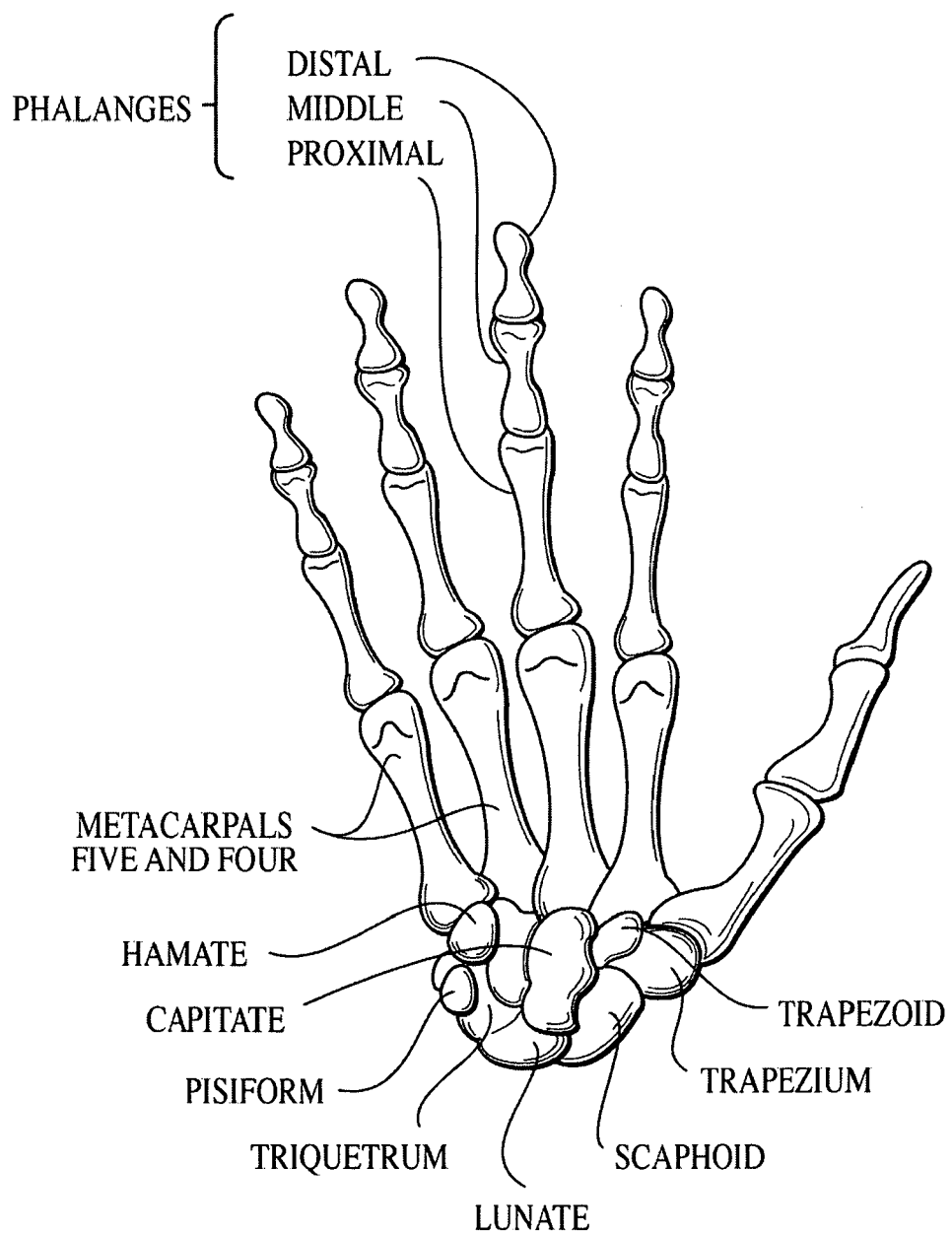
FIG. 7 is a skeletal view of the palmar aspect of the right hand.

To initiate treatment, the pressure source 26 is activated, causing the pressure element 24 to apply force to the longitudinal central dorsal region of the hand 40, that is balanced and opposed by separate forces applied in an opposite direction by the thenar and hypothenar sections 12, 14 to their respective areas of the palmar aspect of the hand 40, so as to implement the Porrata principle to widen the carpal canal and provide treatment of carpal tunnel syndrome to the patient. Referring to FIG. 5–7, this arrangement of forces causes the distance between certain carpal bones of the hands to increase, namely the pisiformis and hook of hamate, on one side, and the trapesium scaphoid, on the other side, thereby stretching the carpal ligament and the flexor retinaculum.

The pressure may be maintained at a constant level for a period of time to induce permanent or semi-permanent elongation of the carpal ligament and the flexor retinaculum, thereby increasing the diameter of the carpal tunnel and decreasing the cause and symptoms of carpal tunnel syndrome. Optional carpal tunnel treatment protocols using the apparatus 8 may consist of applying either constant or varying pressure to the central longitudinal dorsal aspect of the hand for predetermined periods of time at preferably regular intervals. The design of the apparatus 8 is such that, once given proper instruction, treatment can be administered by the patient without the aid of a physician or other assistant. The pressure monitor 30 ensures that the forces applied to the hand 40 can be accurately and easily monitored and duplicated. In addition, the forces can be adjusted while the apparatus 8 is fully mounted on the hand 40. As mentioned above, the apparatus 8 optionally includes a device for limiting the maximum amount of pressure that can be delivered by the pressure element 24, to prevent accidental over-stressing of the carpal ligament and flexor retinaculum.

The wide distribution of forces applied to the hand ensures the comfort of the appliance during treatment, minimizes any detrimental effects of the pressure to the epidermis, and increases the length of time for which the apparatus 8 can be used.

Thus, while there have been shown and described and pointed out fundamental novel features of the invention as applied to preferred embodiments thereof, it will be understood that various omissions and substitutions and changes in the form and details of the devices and methods illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. It is the intention, therefore, to be limited only as indicated by the scope of the claims appended hereto.

We claim:

1. An apparatus for treating carpal tunnel syndrome in a person's hand, the hand having a longitudinal axis, a palmar aspect with thenar and hypothenar regions, and a dorsal region opposed to the palmar aspect, the apparatus comprising:
    a thenar portion having a first top section, and a first bottom section configured for contacting and retaining the thenar region of the hand, wherein the first bottom section comprises a first longitudinal edge positioned along and in contact with the palmar aspect of the hand;
    a hypothenar portion, positioned parallel to the thenar portion, having a second top section, and a second bottom section configured for contacting and retaining the hypothenar region of the hand, wherein the second bottom section comprises a second longitudinal edge positioned along and in contact with the palmar aspect of the hand, and wherein at least one of the first and second bottom sections is semicircular in cross section and configured such that at least one of the respective first and second edges is oriented toward the palmar aspect of the hand;
    a hole defined in said thenar portion between said first top and said first bottom sections, positioned and configured to receive a thumb of the hand when the hand is placed within the apparatus;
    a dorsal portion positioned between, and connected to, said first and second top sections; and
    pressure means, disposed along said dorsal portion so as to contact the dorsal region of the hand when the thenar and hypothenar regions of the hand are retained by said respective first and second bottom sections, for selectively applying pressure to the dorsal region of the hand, such that when said pressure means are activated, a first distributed force is applied to the central dorsal region of the hand between said thenar and hypothenar regions, said first force being balanced and opposed by a second and third forces applied to the thenar and hypothenar regions of the palmar aspect by said first and second bottom sections in response to said first force, to thereby cause the carpal bones to separate and to stretch the carpal ligament and flexor retinaculum, and to thereby effectuate enlargement of the diameter of the carpal tunnel.

2. The apparatus of claim 1, wherein said thenar, hypothenar and dorsal portions are formed as an elongated unitary housing.

3. The apparatus of claim 1, wherein at least one of said thenar, hypothenar and dorsal portions is composed of a substantially rigid material.

4. The apparatus of claim 1, wherein said pressure means further comprise: a pressure element positioned along said dorsal portion to contact a central longitudinal dorsal region of the hand; and active pressure means, connected to the pressure element, for selectively activating said pressure element to deliver said pressure to apply said first distributed force to the dorsal aspect of the hand.

5. The apparatus of claim 4, wherein said pressure element further comprises a resilient pad for distributing said pressure along the longitudinal dorsal region.

6. The apparatus of claim 4, further comprising pressure control means, connected to said pressure means, for selecting and varying a magnitude of said pressure to thereby select and vary said first distributed force during treatment.

7. The apparatus of claim 6, further comprising pressure monitoring means, connected to said pressure means, for monitoring said magnitude of said pressure during treatment.

8. The apparatus of claim 7, further comprising a timer for monitoring a length of time period of the treatment.

9. The apparatus of claim 8, wherein said timer further comprises: means for selectively defining a length of said time period of the treatment prior to treatment, means for monitoring said time period during treatment, and means for issuing an alert after expiration of said time period.

10. The apparatus of claim 7, wherein at least one of said active pressure means and said pressure monitoring means are positioned at one of said thenar, hypothenar and dorsal portions.

11. The apparatus of claim 7, wherein said pressure element comprises an inflatable bladder, and wherein said active pressure means comprises a controllable source of pressurized gas or liquid connected to said inflatable bladder.

12. The apparatus of claim 11, wherein said pressure monitoring means is a pressure gauge connected to one of said controllable source and said inflatable bladder.

13. An apparatus for treating carpal tunnel syndrome in a person's hand, the hand having a longitudinal axis, a palmar aspect with thenar and hypothenar regions, and a dorsal region opposed to the palmar aspect, the apparatus comprising:
    an elongate unitary housing comprising: a thenar portion having a first top section, and a first bottom section configured for contacting and retaining the thenar region of the hand, wherein the first bottom section comprises a first longitudinal edge positioned along and in contact with the palmar aspect of the hand;
    a hypothenar portion, positioned parallel to the thenar portion, having a second top section, and a second bottom section configured for contacting and retaining the hypothenar region of the hand, wherein the second bottom section comprises a second longitudinal edge positioned along and in contact with the palmar aspect of the hand, and wherein at least one of the first and second bottom sections is semicircular in cross section and configured such that at least one of the respective first and second edges is oriented toward the palmar aspect of the hand;
    a hole defined in said thenar portion between said first top and said first bottom sections, positioned and configured to receive a thumb of the hand when the hand is placed within the apparatus;

a dorsal portion positioned between, and connected to, said first and second top sections;

a pressure element, disposed along said dorsal portion so as to contact the dorsal region of the hand when the thenar and hypothenar regions of the hand are retained by said respective first and second bottom sections;

and a pressure source connected to the pressure element, for selectively applying pressure to the dorsal region of the hand, such that when said pressure means are activated, a first distributed force is applied to the central dorsal region of the hand between said thenar and hypothenar regions, said first force being balanced and opposed by a second and third forces applied to the thenar and hypothenar regions of the palmar aspect by said first and second bottom sections in response to said first force, to thereby cause the carpal bones to separate and to stretch the carpal ligament and flexor retinaculum, and to thereby effectuate enlargement of the diameter of the carpal tunnel.

14. The apparatus of claim 13, wherein the pressure source is positioned along the dorsal portion.

15. The apparatus of claim 13, wherein at least one of said thenar, hypothenar and dorsal portions is composed of a substantially rigid material.

16. The apparatus of claim 13, further comprising a pressure monitor connected to said pressure element, for monitoring said magnitude of said pressure during treatment.

17. The apparatus of claim 13, further comprising a timer for monitoring a length of time period of the treatment.

18. The apparatus of claim 17, wherein said timer further comprises means for selectively defining a length of said time period of the treatment prior to treatment, means for monitoring said time period during treatment, and means for issuing an alert after expiration of said time period.

19. The apparatus of claim 13, wherein said pressure element further comprises a resilient pad for distributing said pressure along the longitudinal dorsal region.

20. The apparatus of claim 13, wherein said pressure element comprises an inflatable bladder, and wherein said pressure source comprises a controllable source of pressurized gas or liquid connected to said inflatable bladder.

21. The apparatus of claim 20 further comprising a pressure gauge connected to one of said controllable source and said inflatable bladder.

* * * * *